United States Patent
Tokita et al.

(10) Patent No.: US 9,339,582 B2
(45) Date of Patent: May 17, 2016

(54) ABSORBENT AND ABSORPTIVE ARTICLE

(75) Inventors: Norihiro Tokita, Kanonji (JP); Takayoshi Konishi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 1 day.

(21) Appl. No.: 14/348,523

(22) PCT Filed: Aug. 8, 2012

(86) PCT No.: PCT/JP2012/070236
§ 371 (c)(1),
(2), (4) Date: Mar. 28, 2014

(87) PCT Pub. No.: WO2013/046946
PCT Pub. Date: Apr. 4, 2013

(65) Prior Publication Data
US 2014/0343524 A1    Nov. 20, 2014

(30) Foreign Application Priority Data
Sep. 30, 2011  (JP) .................................. 2011-216542

(51) Int. Cl.
*A61F 13/53*  (2006.01)
*A61L 15/42*  (2006.01)
*A61L 15/40*  (2006.01)
*D21H 11/12*  (2006.01)

(52) U.S. Cl.
CPC ............... *A61L 15/425* (2013.01); *A61F 13/53* (2013.01); *A61L 15/40* (2013.01); *A61L 15/42* (2013.01); *D21H 11/12* (2013.01); *A61F 2013/530007* (2013.01); *A61F 2013/530343* (2013.01)

(58) Field of Classification Search
CPC ................... A61F 13/53; A61F 2013/530007; A61F 2013/530343; A61F 2013/530379
See application file for complete search history.

(56) References Cited

U.S. PATENT DOCUMENTS

| | | | |
|---|---|---|---|
| 4,468,428 A | 8/1984 | Early et al. | |
| 4,495,082 A | 1/1985 | Mita et al. | |
| 5,466,232 A | 11/1995 | Cadieux et al. | |
| 5,542,940 A | 8/1996 | Jonker | |
| 5,645,916 A | 7/1997 | Oathout | |
| 6,063,982 A | 5/2000 | Martin et al. | |
| 6,074,523 A * | 6/2000 | Mizobuchi et al. | 162/91 |
| 6,642,428 B1 * | 11/2003 | Kurata | A61F 13/15203 604/364 |
| 6,723,430 B2 * | 4/2004 | Kurata | A61F 13/15211 428/378 |
| 2003/0135179 A1 | 7/2003 | Krautkramer et al. | |
| 2004/0214499 A1 * | 10/2004 | Qin et al. | 442/414 |
| 2004/0253890 A1 * | 12/2004 | Ostgard et al. | 442/153 |
| 2004/0253892 A1 * | 12/2004 | Baker et al. | 442/327 |
| 2011/0034891 A1 * | 2/2011 | Jiang et al. | 604/358 |
| 2012/0048916 A1 | 3/2012 | Konishi et al. | |

(Continued)

FOREIGN PATENT DOCUMENTS

| | | |
|---|---|---|
| EP | 2689759 A1 | 1/2014 |
| EP | 2692319 A1 | 2/2014 |
| JP | 55133249 A | 10/1980 |

(Continued)

*Primary Examiner* — Susan Su

(74) *Attorney, Agent, or Firm* — Hauptman Ham, LLP

(57) ABSTRACT

In order to provide an absorbent, which contains no wood pulp and wood pulp and has improved liquid absorbability and improved liquid retention ability, and an absorptive article provided with the absorbent, no wood pulp having a settling time in water of 2-5 sec is used in an absorbent that contains no wood pulp and wood pulp.

20 Claims, 5 Drawing Sheets

(56) References Cited

U.S. PATENT DOCUMENTS

| | | | |
|---|---|---|---|
| 2014/0031778 A1* | 1/2014 | Konishi | A61F 13/53 604/374 |
| 2014/0141970 A1* | 5/2014 | Konishi | A61F 13/53 502/404 |

FOREIGN PATENT DOCUMENTS

| | | |
|---|---|---|
| JP | 2168949 A | 6/1990 |
| JP | 788126 A | 4/1995 |
| JP | 7505454 A | 6/1995 |
| JP | 7236653 A | 9/1995 |
| JP | 2003147690 A | 5/2003 |
| JP | 2005160717 A | 6/2005 |
| JP | 200913521 A | 1/2009 |
| JP | 2010136969 A | 6/2010 |
| JP | 2011-15886 A | 1/2011 |

\* cited by examiner (a)

(b)

(a)

(b)

(c)

ABSORBENT AND ABSORPTIVE ARTICLE

RELATED APPLICATIONS

The present application is a National Phase of International Application Number PCT/JP2012/070236, filed Aug. 8, 2012, which claims priority to Japanese Application Number 2011-216542, filed Sep. 30, 2011.

TECHNICAL FIELD

The present invention relates to an absorber and to an absorbent article comprising the absorber.

BACKGROUND ART

In the past, non-wood pulp and wood pulp have been used as materials for absorbers in disposable absorbent articles such as sanitary and hygiene articles (see PTL 1, for example). In PTL 1, the water retention of the absorber under pressure or compression is increased by blending pith-containing bagasse pulp and wood pulp, which differ from each other in bulk density, in a prescribed ratio, thereby adjusting the bulk density.

CITATION LIST

Patent Literature

[PTL 1] Japanese Unexamined Patent Publication No. S55-133249

DISCLOSURE OF THE INVENTION

Technical Problem

However, improvement has been desired for absorbers comprising non-wood pulp and wood pulp, from the viewpoint of increasing fluid absorption and fluid retention.

It is therefore an object of the present invention to provide an absorber comprising non-wood pulp and wood pulp and exhibiting increased fluid absorption and fluid retention, and an absorbent article comprising the absorber.

Solution to Problem

In order to solve the problem described above, the invention provides an absorber comprising non-wood pulp and wood pulp, wherein the settling time in water of the non-wood pulp is 2 to 5 seconds.

In addition, the invention provides an absorbent article comprising a liquid-permeable sheet, a liquid-impermeable sheet, and an absorber situated between the liquid-permeable sheet and the liquid-impermeable sheet, wherein the absorber is an absorber according to the invention.

Non-wood pulp with a settling time in water of 2 to 5 seconds has a porous structure (hollow structure), while wood pulp does not have a porous structure (hollow structure). Since specific surface area and porosity of non-wood pulp with a porous structure are larger than those of wood pulp, fluid absorption of non-wood pulp is greater than that of wood pulp. On the other hand, since fluid retention of a porous structure is weaker, fluid retention under a normal condition (non-pressure condition) of non-wood pulp with a porous structure is equal to or less than that of wood pulp. However, since porosity under pressure (compression) of non-wood pulp with a porous structure is greater than that of wood pulp, fluid retention under pressure of non-wood pulp is greater than that of wood pulp.

Thus, fluid absorption and fluid retention under pressure of non-wood pulp with a porous structure are superior to those of wood pulp, whereas fluid retention under a normal condition (non-pressure condition) of non-wood pulp is inferior to that of wood pulp. In addition, fluid retention under centrifugal dewatering of non-wood pulp with a porous structure is inferior to that of wood pulp.

Consequently, the absorber of the invention comprises non-wood pulp having a settling time in water of 2 to 5 seconds, and wood pulp, and therefore exhibits excellent fluid absorption of the non-wood pulp and excellent fluid retention under pressure of the non-wood pulp in addition to excellent fluid retention under a normal condition (non-pressure condition) of the wood pulp. This allows the absorber of the invention to rapidly absorb fluids while preventing fluid exudation (rewetting) when pressure is applied to the absorber.

Furthermore, since the fluid retention of the porous structure of the non-wood pulp is weak, fluids rapidly transfer from the non-wood pulp to the wood pulp. Therefore, the absorber of the invention can exhibit excellent fluid absorption even when fluids are repeatedly absorbed into the absorber of the invention. For example, when after 40 mL of artificial urine is absorbed into the absorber, additional 40 mL of artificial urine is added to the absorber at a rate of 8 mL/sec, the absorber can exhibit excellent fluid absorption characterized by an absorption time of 10 seconds or shorter. The artificial urine used may be 0.9% physiological saline, for example.

In the absorber of the invention, the non-wood pulp preferably has one or more of the following properties, in addition to the property of a settling time in water of 2 to 5 seconds.

The apparent bulk density of the non-wood pulp is 0.04 to 0.07 g/cm$^3$.

The artificial urine absorption of the non-wood pulp is at least 20 times the mass of the non-wood pulp.

The mean fiber size of the non-wood pulp is 8 to 25 μm.

The lignin content of the non-wood pulp is 0.5 mass % or less.

Non-wood pulp with an apparent bulk density of 0.04 to 0.07 g/cm$^3$ has larger specific surface area and porosity than wood pulp, and therefore has more excellent fluid absorption and fluid retention under pressure than wood pulp.

Non-wood pulp with an artificial urine absorption of at least 20 times the mass of the non-wood pulp has more excellent fluid absorption than wood pulp.

Non-wood pulp with a mean fiber size of 8 to 25 μm has a greater number of fibers (i.e. volume) per unit mass than wood pulp, and therefore has smaller apparent bulk density and larger specific surface area and porosity than wood pulp. In addition, the distances between fibers in the non-wood pulp are smaller than in wood pulp, and the capillary action of the non-wood pulp is greater than that of wood pulp. Consequently, non-wood pulp with a mean fiber size of 8 to 25 μm has more excellent fluid absorption and fluid retention under pressure than wood pulp. Furthermore, since increasing the number of fibers increases entanglement between the fibers, the strength of the absorber is maintained even when the weight or thickness of the absorber is reduced.

Non-wood pulp with a lignin content of 0.5 mass % or less prevents increase in fiber size and reduction in hydrophilicity due to lignin, and therefore has more excellent fluid absorption and fluid retention under pressure than wood pulp.

In the absorber of the invention, the non-wood pulp is preferably abaca pulp made from Manila hemp leaf sheath, or banana pulp made from banana stem. By using Manila hemp leaf sheath or banana stem as a starting material, it is possible to simply and efficiently obtain non-wood pulp having the properties described above.

In the absorber of the invention, the abaca pulp is preferably abaca pulp made from a portion near the core of Manila hemp leaf sheath or from a portion between the core and hull of Manila hemp leaf sheath. By using the portion near the core of Manila hemp leaf sheath or from the portion between the core and hull of Manila hemp leaf sheath as a starting material, it is possible to simply and efficiently obtain non-wood pulp having the properties described above.

In the absorber of the invention, the mass ratio of the non-wood pulp to the wood pulp is preferably 3:1 to 1:3. If the mass ratio of the non-wood pulp to the wood pulp is 3:1 to 1:3, the excellent fluid absorption and fluid retention under pressure of the non-wood pulp and the excellent fluid retention under a normal condition (non-pressure condition) of the wood pulp will both be effectively exhibited.

In the absorber of the invention, the total content of the non-wood pulp and wood pulp is preferably at least 30 mass % of the absorber. If the total content of the non-wood pulp and wood pulp is at least 30 mass % of the absorber, the excellent fluid absorption and fluid retention under pressure of the non-wood pulp and the excellent fluid retention under a normal condition (non-pressure condition) of the wood pulp will both be effectively exhibited.

The absorber of the invention preferably further comprises an absorbent polymer. Because the fluid retention of the porous structure of the non-wood pulp is weak, fluids rapidly transfer from the non-wood pulp into the absorbent polymer. Therefore, if the absorber further comprises an absorbent polymer, the absorber can exhibit excellent fluid absorption even when fluids are repeatedly absorbed into the absorber.

Since the non-wood pulp becomes entrapped between the absorbent polymers, swelling (gel formation) of the absorbent polymers, which occurs when the absorbent polymers absorb fluids, does not result in coalescence between the swelled absorbent polymers. Consequently, the absorbent polymers that have absorbed fluids and become swelled do not become a barrier (gel blocking) when the fluids permeate the absorber. This can prevent the phenomenon of overflowing of the fluids that fail to permeate the absorber (overflow phenomenon).

Effect of the Invention

According to the invention, there are provided an absorber comprising non-wood pulp and wood pulp, and exhibiting increased fluid absorption and fluid retention, and an absorbent article comprising the absorber.

DESCRIPTION OF EMBODIMENTS

There are no particular restrictions on the type and usage of the absorbent article of the invention. For example, absorbent articles include sanitary and hygiene articles such as disposable diapers, sanitary napkins, panty liners, incontinence pads and perspiration sheets, which may be for humans or animals other than humans, such as pets. There are no particular restrictions on the fluid to be absorbed by the absorbent article of the invention, and for example, it may be liquid excreta or body fluid of the user.

Embodiments of the absorbent article of the invention will now be described, using a disposable diaper as an example.

Figure 1:
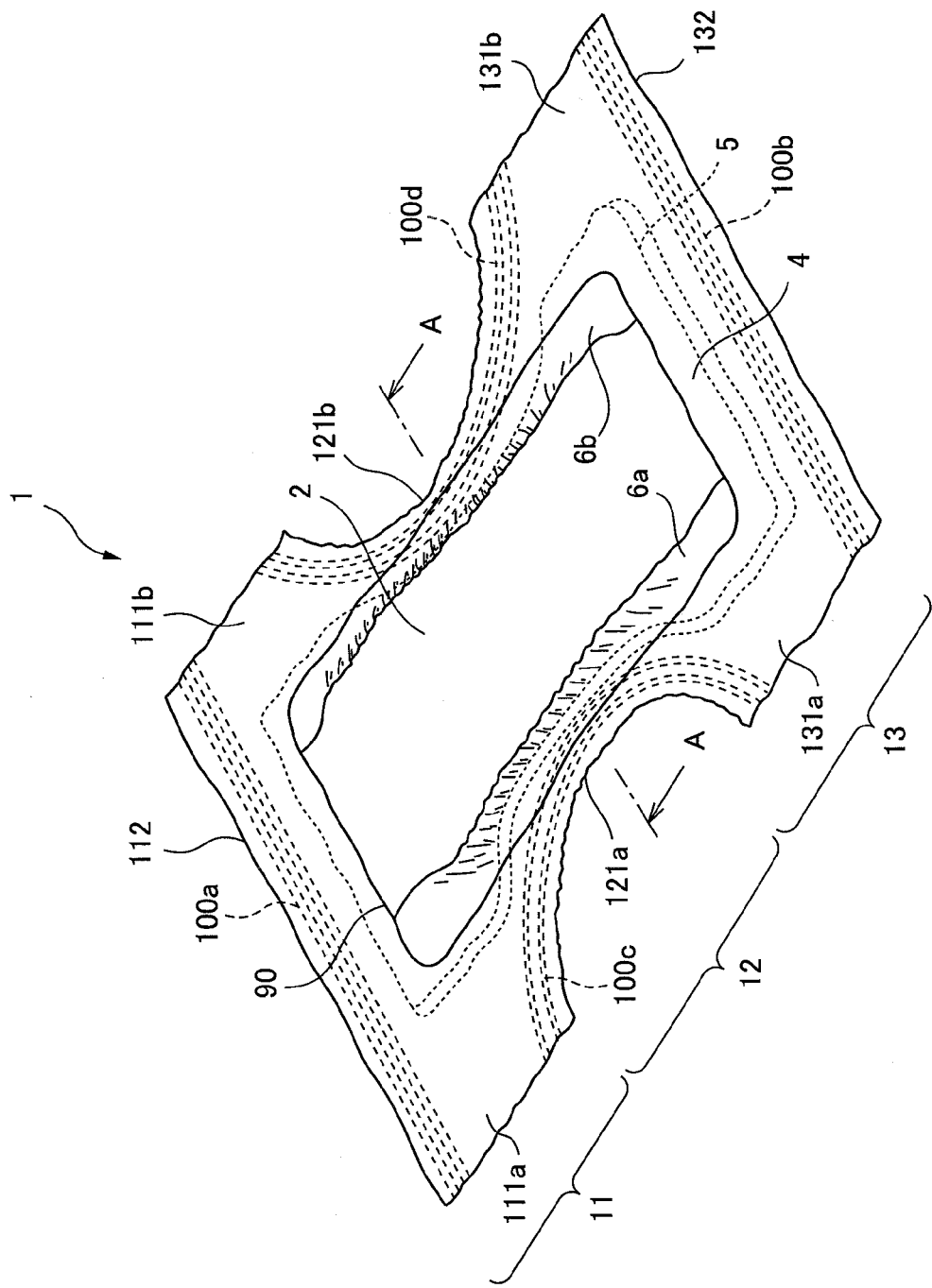
FIG. 1 is a perspective view of a disposable diaper according to an embodiment of the invention, before use (in an outspread state).
Figure 2:
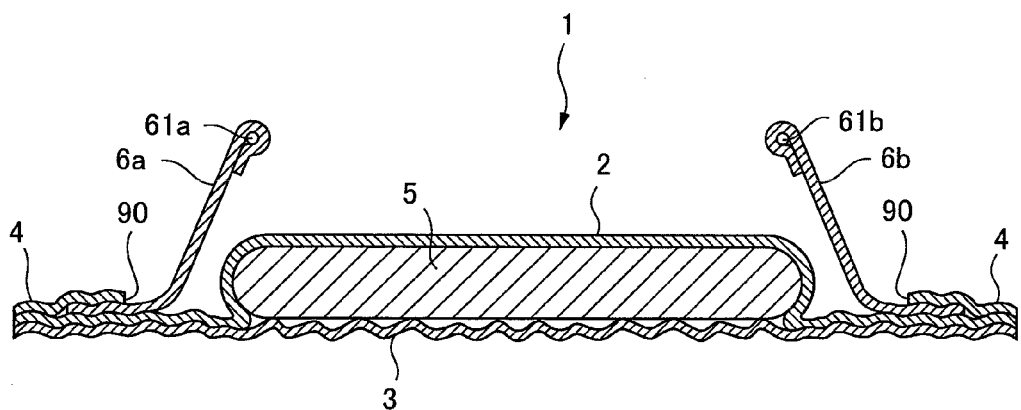
FIG. 2 is a cross-sectional view of the disposable diaper of FIG. 1, along line A-A.

The diaper 1 according to an embodiment of the invention, as shown in FIG. 1 and FIG. 2, comprises a liquid-permeable sheet 2, a liquid-impermeable sheet 3 provided below the liquid-permeable sheet 2, an auxiliary sheet 4 provided above the liquid-permeable sheet 2, and an absorber 5 provided between the liquid-permeable sheet 2 and liquid-impermeable sheet 3. The liquid-permeable sheet 2, liquid-impermeable sheet 3 and auxiliary sheet 4 have hourglass shapes of roughly the same dimensions, while the diaper 1 in an outspread state (before being worn by a user) also has an hourglass shape, as shown in FIG. 1.

Figure 3:
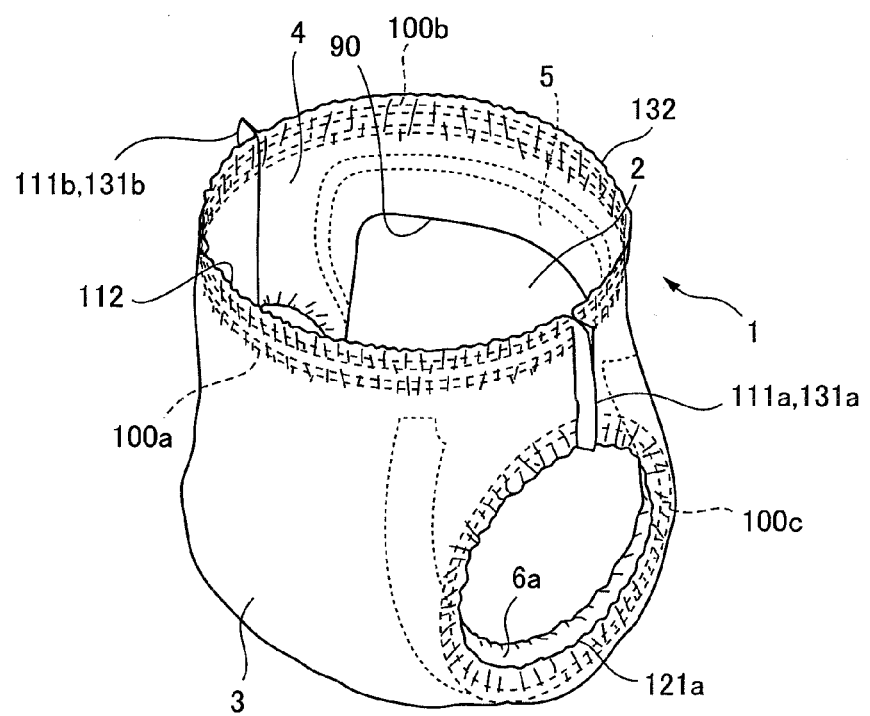
FIG. 3 is a perspective view of the disposable diaper of FIG. 1 during use.

The diaper 1 is worn by a user to absorb liquid excreta of the user. As shown in FIG. 3, it is worn by the user so that the auxiliary sheet 4 is positioned on the inner side (the skin side of the user) and the liquid-impermeable sheet 3 is positioned on the outer side (the clothing side of the user). The liquid excreta to be absorbed is, for example, urine, menstrual blood, vaginal discharge or the like, and will usually be mainly urine.

As shown in FIG. 1, the diaper 1 has a front section 11 that contacts the abdominal region of the user when worn, a middle section 12 that contacts the crotch section of the user when worn, and a back section 13 that contacts the buttocks and/or back of the user when worn. When the diaper 1 is worn by the user, as shown in FIG. 3, both edges 111a, 111b of the front section 11 and both edges 131a, 131b of the back section 13 are connected, and a waist opening is formed by the edge 112 of the front section 11 and the edge 132 of the back section 13. In addition, both edges 121a, 121b of the middle section 12 contact the femoral region of the user, and leg openings are formed by both edges 121a, 121b of the middle section 12. Also, as shown in FIG. 1, elastic members 100a, 100b are provided on the edge 112 of the front section 11 and on the edge 132 of the back section 13 while elastic members 100c, 100d are provided on both edges 121a, 121b of the middle section 12. When the diaper 1 is worn by the user, as shown in FIG. 3, a waist gather is formed in the waist opening by elastic contractive force of the elastic members 100a, 100b, while leg gathers (cuffs on the leg sides) are also formed in the leg openings by the elastic contractive force of the elastic members 100c, 100d.

As shown in FIG. 1 and FIG. 2, an opening 90 is provided at the center of the auxiliary sheet 4, and a portion of the liquid-permeable sheet 2 (the section covering the absorber 5) is exposed through the opening 90 of the auxiliary sheet 4. Liquid excreta of the user enter through the opening 90 of the auxiliary sheet 4, permeate into the absorber 5 through the liquid-permeable sheet 2, and are absorbed by the absorber 5. Leakage of liquid excreta that have been absorbed into the absorber 5 is prevented by the liquid-impermeable sheet 3.

As shown in FIG. 1 and FIG. 2, leakproof cuffs 6a, 6b formed by liquid-impermeable sheets are provided on both sides of the opening 90 of the auxiliary sheet 4. As shown in FIG. 2, one edge of each of the leakproof cuffs 6a, 6b is the anchored end that is sandwiched and anchored between the liquid-permeable sheet 2 and the auxiliary sheet 4, while the other edge is the free end that is exposed through the opening 90 of the auxiliary sheet 4. As shown in FIG. 2, the free ends of the leakproof cuffs 6a, 6b are provided with elastic members 61a, 62b, and when the diaper 1 is worn by a user, the leakproof cuffs 6a, 6b rise upward toward the femoral region of the user on the inner side of the leg openings, as shown in FIG. 3.

The liquid-permeable sheet 2 is a sheet through which liquid excreta of the user can permeate, and it is provided on the side in contact with the skin of the user (especially the crotch section), to improve the feel on the skin when the diaper 1 is worn by the user.

The liquid-permeable sheet 2 is not particularly restricted so long as it allows permeation of liquid excreta of the user. Examples of the liquid-permeable sheet 2 include nonwoven fabrics, woven fabrics, fluid permeation hole-formed synthetic resin films and meshed net-like sheets, with nonwoven fabrics being preferred among these.

The nonwoven fabric may be produced, for example, by forming a web (fleece) and physically or chemically bonding the fibers together, where methods for forming a web include spunbond methods, dry methods (carding methods, spunbond methods, meltblown methods and airlaid methods), and wet methods, and bonding methods include thermal bond methods, chemical bond methods, needle punching methods, stitch bond methods and spunlace methods.

The material, thickness, basis weight and density of the liquid-permeable sheet 2 can be appropriately set in ranges that allow permeation of liquid excreta of the user. When a nonwoven fabric is to be used as the liquid-permeable sheet 2, examples of fibers to be used to form the nonwoven fabric include natural fibers (wool, cotton and the like), regenerated fibers (rayon, acetate and the like), inorganic fibers (glass fibers, carbon fibers and the like), synthetic resin fibers (polyolefins such as polyethylene, polypropylene, polybutylene, ethylene-vinyl acetate copolymer, ethylene-ethyl acrylate copolymer, ethylene-acrylic acid copolymer, and ionomer resins; polyesters such as polyethylene terephthalate, polybutylene terephthalate, polytrimethylene terephthalate and polylactic acid, and polyamides such as nylon). The fibers composing the nonwoven fabric may be made of a single component, or they may be made of composite fibers such as core/sheath fibers, side-by-side fibers or island/sea fibers. The fineness of the fibers composing the nonwoven fabric is preferably 1.0 to 20 dtex and even more preferably 1.2 to 4.4 dtex, and the fiber lengths are preferably 5 to 75 mm and even more preferably 25 to 51 mm. The basis weight of the nonwoven fabric is preferably 10 to 100 g/m$^2$ and even more preferably 20 to 35 g/m$^2$, and the fiber density is preferably 0.001 to 0.2 g/cm$^3$ and even more preferably 0.015 to 0.08 g/cm$^3$. The thickness of the nonwoven fabric under a load of 3 g/cm$^2$ is preferably 0.1 to 3 mm and even more preferably 0.5 to 2 mm.

The liquid-impermeable sheet 3 is a sheet that does not allow permeation of liquid excreta of the user, and it is provided on the side in contact with the clothing of the user to prevent leakage of liquid excreta that has been absorbed in the absorber 5. The liquid-impermeable sheet 3 is preferably air-permeable in addition to being liquid-impermeable, in order to reduce mustiness when worn.

The liquid-impermeable sheet 3 is not particularly restricted so long as it does not allow permeation of liquid excreta of the user. Examples of the liquid-impermeable sheet 3 include waterproof treated nonwoven fabrics (for example, point bond nonwoven fabrics, spunbond nonwoven fabrics and spunlace nonwoven fabrics), synthetic resin (for example, polyethylene, polypropylene and polyethylene terephthalate) films, and composite sheets of nonwoven fabrics and synthetic resin films.

The auxiliary sheet 4 may be liquid-permeable or liquid-impermeable, but will usually be liquid-impermeable. Examples of the auxiliary sheet 4 include waterproof treated nonwoven fabrics (for example, point bond nonwoven fabrics, spunbond nonwoven fabrics and spunlace nonwoven fabrics), synthetic resins (for example, polyethylene, polypropylene and polyethylene terephthalate) films, and composite sheets of nonwoven fabrics and synthetic resin films.

The absorber 5 is an absorbing layer composed of a mixed material comprising non-wood pulp and wood pulp. The absorber 5 is covered with tissue (not shown) to prevent disintegration of the absorber 5, but the tissue may be omitted if there is no need to prevent disintegration of the absorber 5.

The settling time in water of the non-wood pulp in the absorber 5 is 2 to 5 seconds and preferably 2.5 to 4 seconds.

If non-wood pulp has a porous structure (hollow structure), air will be included in the porous structure, and therefore the settling time in water of the non-wood pulp is lengthened (that is, the settling velocity in water is slowed). Thus, non-wood pulp with a settling time in water of 2 to 5 seconds is thought to have a porous structure (hollow structure). Since non-wood pulp with a porous structure has larger specific surface area and porosity than wood pulp, the fluid absorption of the non-wood pulp is greater than that of wood pulp. On the other hand, the fluid retention of a porous structure is weaker, and therefore the fluid retention of non-wood pulp with a porous structure is equal to or less than that of wood pulp. However, since non-wood pulp with a porous structure also has a greater porosity under pressure (compression) than wood pulp, the fluid retention under pressure of the non-wood pulp is greater than that of wood pulp. Thus, the fluid absorption and fluid retention under pressure of non-wood pulp with a porous structure are superior to those of wood pulp, but the fluid retention under a normal condition (non-pressure condition) of the non-wood pulp is inferior to that of the wood pulp.

Consequently, the absorber 5 comprises non-wood pulp having a settling time in water of 2 to 5 seconds, and wood pulp, and therefore exhibits both the excellent fluid absorption and fluid retention under pressure of the non-wood pulp and the excellent fluid retention under a normal condition (non-pressure condition) of the wood pulp. This allows the absorber 5 to rapidly absorb liquid excreta of the user while preventing exudation of liquid excreta (rewetting) when pressure is applied to the absorber 5.

Furthermore, since the fluid retention of the porous structure of the non-wood pulp is weak, liquid excreta rapidly transfer from the non-wood pulp to the wood pulp. Therefore, the absorber 5 exhibits excellent fluid absorption even when liquid excreta are repeatedly absorbed into the absorber 5. For example, when after 40 mL of artificial urine is absorbed into the absorber 5, additional 40 mL of artificial urine is added to the absorber 5 at a rate of 8 mL/sec, the absorber 5 exhibits excellent fluid absorption characterized by an absorption time of 10 seconds or shorter. The artificial urine used may be 0.9% physiological saline, for example.

The settling time in water of the non-wood pulp is the time from contact of the non-wood pulp with the water surface until the non-wood pulp sinks under the water surface, and specifically it is the time measured in the following manner. A 5.0 g portion of non-wood pulp is evenly packed into a cylindrical basket (weight: 3 g, diameter: 50 mm, depth: 80 mm). The basket is formed of copper wires (diameter: 0.4 mm), the spacing between copper wires being 20 mm. Ion-exchanged water is added until the water depth reaches 200 mm in a 2 L beaker. The basket containing the packed non-wood pulp is laid on its side and dropped from a height of 10 mm from the surface of water in the 2 L beaker, and the time from contact of the basket with the water surface until the basket sinks under the water surface (sec) is measured and recorded as the settling time in water (sec).

The non-wood pulp in the absorber 5 preferably has one or more of the following properties, in addition to the property of a settling time in water of 2 to 5 seconds.

The apparent bulk density of the non-wood pulp is 0.04 to 0.07 g/cm$^3$.

The artificial urine absorption of the non-wood pulp is at least 20 times the mass of the non-wood pulp.

The mean fiber size of the non-wood pulp is 8 to 25 µm (preferably 10 to 20 µm).

The lignin content of the non-wood pulp is 0.5 mass % or less (preferably 0.3 mass % or less).

Non-wood pulp with an apparent bulk density of 0.04 to 0.07 g/cm$^3$ has larger specific surface area and porosity than wood pulp, and therefore has more excellent fluid absorption and fluid retention under pressure than wood pulp. If the apparent bulk density of the non-wood pulp is less than 0.04 g/cm$^3$, the strength and shape retention of the absorber 5 may be insufficient, while if the apparent bulk density of the non-wood pulp is greater than 0.07 g/cm$^3$, the fluid absorption of the absorber 5 may be insufficient.

The apparent bulk density of the non-wood pulp is calculated in the following manner. After layering 10 g of non-wood pulp at 100 mm×100 mm, a 100 mm×100 mm plate was laid thereover and a weight with a 100 g load was set on the plate. The thickness of the layered pulp at 10 seconds after placement of the weight was used as the apparent bulk (cm$^3$), and the apparent bulk density (g/cm$^3$) was calculated.

Non-wood pulp having an artificial urine absorption of at least 20 times the mass of the non-wood pulp has more excellent fluid absorption than wood pulp. If the artificial urine absorption of the non-wood pulp is less than 20 times the mass of the non-wood pulp, the fluid absorption will be similar to that of wood pulp, and therefore the function and effect of the non-wood pulp will be reduced. When measuring the artificial urine absorption, the artificial urine used is 0.9% physiological saline, for example.

Non-wood pulp with a mean fiber size of 8 to 25 µm has a greater number of fibers (i.e. volume) per unit mass than wood pulp, and therefore the apparent bulk density of the non-wood pulp is smaller than that of wood pulp and the specific surface area and porosity of the non-wood pulp are larger than those of wood pulp. In addition, the distances between fibers in the non-wood pulp are smaller than in wood pulp, and the capillary action of the non-wood pulp is greater than that of wood pulp. Consequently, non-wood pulp with a mean fiber size of 8 to 25 µm has more excellent fluid absorption and fluid retention under pressure than wood pulp. Furthermore, since increasing the number of fibers increases entanglement between the fibers, the strength of the absorber 5 is maintained even when the weight or thickness of the absorber 5 is reduced.

Non-wood pulp with a lignin content of 0.5 mass % or less prevents increase in fiber size and reduction in hydrophilicity due to lignin, and has more excellent fluid absorption and fluid retention under pressure than wood pulp.

Examples of starting materials for the wood pulp include N-material (conifer) and L-material (broadleaf tree). The wood pulp can be produced by removing the bark from the wood trunk and then subjecting it to mechanical, semi-chemical or chemical treatment, either directly, or after conversion to chips.

Examples of common starting materials for the non-wood pulp include linter, Manila hemp, kenaf, esparto grass, straw, bamboo and banana. Manila hemp leaf sheath or banana stem is preferred as a starting material in order to simply and efficiently obtain non-wood pulp having the properties described above. When Manila hemp leaf sheath is used as a starting material, it is preferred to use a portion near the core of Manila hemp leaf sheath or from a portion between the core and hull of Manila hemp leaf sheath.

Figure 6:
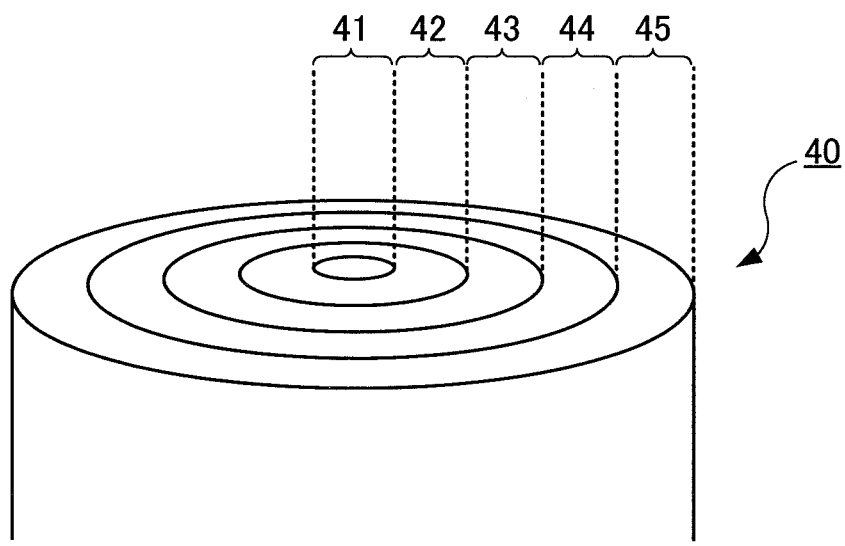
FIG. 6 is a diagram for illustration of the cross-sectional structure of Manila hemp leaf sheath.

Manila hemp leaf sheath will now be described with reference to FIG. 6. As shown in FIG. 6, the cross-sectional structure of Manila hemp leaf sheath 40 is classified as follows: a core 41, a first layer 42, a second layer 43, a third layer 44 and an outermost layer 45. The portion near the core of Manila hemp leaf sheath corresponds to the area near the core of the Manila hemp leaf sheath 40 (the first layer 42 and the second layer 43), while the portion between the core and hull of Manila hemp leaf sheath corresponds to the area near the outermost layer 45 of the Manila hemp leaf sheath 40 (the third layer 44).

Abaca fiber made from Manila hemp is classified as grade AD, EF, S2 or S3, based on the portion of Manila hemp used as a starting material. AD is abaca fiber made from the first layer 42 of Manila hemp 40, and it is pure white glossy fiber. EF is abaca fiber made from the second layer 43 of Manila hemp 40, and it is fiber from the soft pure fiber center portion, having a light ivory color. S2 is abaca fiber made from the third layer 44 of Manila hemp 40, and it has a light ochre color or light violet color. S3 is abaca fiber made from the outermost layer 45 of Manila hemp 40, and it has a dark red or violet color, and is mainly used in rope.

Abaca fiber made from Manila hemp can also be classified as grade I, G or H, based on the portion of the Manila hemp used as a starting material. I is abaca fiber made from the second layer 43 of Manila hemp 40, and it has a pale yellow color. G is abaca fiber made from the third layer 44 of Manila hemp 40, and it has a dull, dark white color and tends to form bundles. H is abaca fiber made from the outermost layer 45 of Manila hemp 40, and it has a nearly black or dark brown color and is mainly used in rope.

Abaca fiber made from Manila hemp can also be classified as grade JK or M1, based on the portion of the Manila hemp used as a starting material. JK is abaca fiber made from the third layer 44 of Manila hemp 40, and it is tan or light-green colored and is used mainly as pulp. M1 is abaca fiber made from the outermost layer 45 of Manila hemp 40, and it is dark brown to black fiber and is mainly used in rope.

Abaca fiber made from the portion near the core of Manila hemp leaf sheath corresponds to abaca fiber AD, EF or I, while abaca fiber made from the portion between the core and hull of Manila hemp leaf sheath corresponds to abaca fiber S2, G or JK. Abaca fiber made from Manila hemp hull corresponds to abaca fiber S3, H or M1.

The mass ratio of the non-wood pulp to the wood pulp in the absorber 5 may be appropriately adjusted according to the properties to be exhibited by the absorber 5 (for example, absorption properties and lightweight properties), but it is preferably 3:1 to 1:3 and even more preferably 2:1 to 1:2. If the mass ratio of both is within this range, the excellent fluid absorption and fluid retention under pressure of the non-wood pulp and the excellent fluid retention under a normal condition (non-pressure condition) of the wood pulp will both be effectively exhibited.

The total content of the non-wood pulp and wood pulp may be appropriately adjusted according to the properties to be exhibited by the absorber 5 (for example, absorption properties and lightweight properties), but it is preferably at least 30 mass % of the absorber 5 and more preferably at least 50 mass % of the absorber 5. If the total content of both is within this range, the excellent fluid absorption and fluid retention under pressure of the non-wood pulp and the excellent fluid retention under a normal condition (non-pressure condition) of the wood pulp will both be effectively exhibited.

The absorber 5 preferably comprises an absorbent polymer in addition to the non-wood pulp and wood pulp. Because the fluid retention of the porous structure of the non-wood pulp is weak, liquid excreta rapidly transfer from the non-wood pulp into the absorbent polymer. Therefore, if the absorber 5 further comprises an absorbent polymer, the absorber 5 can exhibit excellent fluid absorption even when liquid excreta are repeatedly absorbed into the absorber 5. Since the non-wood pulp becomes entrapped between the absorbent polymers, swelling (gel formation) of the absorbent polymers, which occurs when the absorbent polymers absorb fluids, does not result in coalescence between the swelled absorbent polymers. Consequently, the absorbent polymers that have absorbed liquid excreta and become swelled do not become a barrier (gel blocking) when the liquid excreta permeate the absorber 5. This can prevent the phenomenon of overflowing of the liquid excreta that fail to permeate the absorber 5 (overflow phenomenon).

The absorbent polymer is preferably a super-absorbent polymer. The super-absorbent polymer is a hydrophilic polymer with a crosslinked structure, examples of which include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulose-based polymers, among which polyacrylic acid salt-based (and especially sodium polyacrylate-based) polymers are preferred.

The amount of absorbent polymer in the absorber 5 may be appropriately adjusted according to the properties to be exhibited by the diaper 1 (for example, absorption properties and lightweight properties), but it will usually be 20 to 80 mass %, preferably 30 to 70 mass % and even more preferably 40 to 60 mass % of the absorber 5. If the absorbent polymer content is within this range, both of the functions of absorption (liquid absorption speed) and fluid retention (the action of preventing rewetting) of the diaper 1 will be improved.

The thickness, basis weight and density of the absorber 5 may be appropriately adjusted according to the properties to be exhibited by the diaper 1 (for example, absorption properties and lightweight properties), but the thickness will usually be 1 to 10 mm, preferably 2 to 8 mm and more preferably 3 to 7 mm, the basis weight will usually be 100 to 1000 g/m$^2$, preferably 200 to 800 g/m$^2$ and more preferably 400 to 600 g/m$^2$, and the density will usually be 0.01 to 1 g/cm$^3$, preferably 0.03 to 0.5 g/cm$^3$, and more preferably 0.05 to 0.3 g/cm$^3$. If the thickness, basis weight and density are in these ranges, both of the functions of absorption (liquid absorption speed) and fluid retention (the action of preventing rewetting) of the diaper 1 will be improved.

The diaper 1 can be produced by a common method, and bonding between sheets may be accomplished using an adhesive such as a hot-melt adhesive.

EXAMPLES

The invention will now be explained in greater detail by the following examples.

Test Examples 1 to 7

(1) Preparation of Ground Pulp 1

Test Example Product 1

Abaca BKP (AK104 by Ogura Trading Co., Ltd.) obtained from the portion near the core of Manila hemp leaf sheath, was pulverized into a fibrous state to prepare ground pulp 1. BKP stands for Bleached Kraft Pulp (the same hereinafter).

(2) Preparation of Ground Pulp 2

Test Example Product 2

Abaca BKP (AK102 by Ogura Trading Co., Ltd.) obtained from the portion between the core and hull of Manila hemp leaf sheath, was pulverized into a fibrous state to prepare ground pulp 2.

(3) Preparation of Ground Pulp 3

Test Example Product 3

Abaca BKP (AK101 by Ogura Trading Co., Ltd.) obtained from the portion near the hull of Manila hemp leaf sheath, was pulverized into a fibrous state to prepare ground pulp 3.

(4) Preparation of Ground Pulp 4

Test Example Product 4

Banana BKP (Ogura Trading Co., Ltd.) obtained from banana stem, was pulverized into a fibrous state to prepare ground pulp 4.

(5) Preparation of Ground Pulp 5

Test Example Product 5

Ground pulp 5 was prepared by pulverizing wood pulp (needle bleached soft wood kraft pulp (NBKP)) obtained from conifer (Douglas fir), into a fibrous form.

(6) Preparation of Ground Pulp 6

Test Example Product 6

Bagasse BKP (Ogura Trading Co., Ltd.) obtained from sugar cane (bagasse), was pulverized into a fibrous state to prepare ground pulp 6.

(7) Preparation of Ground Pulp 7

Test Example Product 7

Kenaf BKP (Ogura Trading Co., Ltd.) obtained from kenaf (bast), was pulverized into a fibrous state to prepare ground pulp 7.

(8) Evaluation Test of ground Pulps 1 to 7

Test Example Products 1 to 7

The mean fiber size (µm), lignin content (wt %), settling time (sec), fiber specific gravity (g/cm$^3$), apparent bulk density (g/cm³), fluid absorption (g/g), fluid absorption under pressure (g/g) and fluid retention (g/g) of the ground pulps 1 to 7 were measured by the following methods.

<Mean Fiber Size>

A Fiber Lab 3.8 Kajaani fiber length analyzer by Metso Automation Co. was used to measure the fiber sizes of approximately 20,000 fibers in pulp, and the mean fiber size (μm) of the pulp was calculated.

<Lignin Content>

The lignin content (wt %) in pulp was measured according to the method of P. J. Van Soest et al. (Proc. Nutr. Soc., 32 123 (1973)).

<Settling Time>

A 5.0 g portion of pulp fiber was evenly packed into a cylindrical basket (weight: 3 g, diameter: 50 mm, depth: 80 mm). The basket was formed of copper wires (diameter: 0.4 mm), the spacing between copper wires being 20 mm. Ion-exchanged water was added until the water depth reached 200 mm in a 2 L beaker. The basket containing the packed pulp fiber was laid on its side and dropped from a height of 10 mm from the surface of water in the 2 L beaker, and the time from contact of the basket with the water surface until the basket sunk under the water surface (sec) was measured and recorded as the settling time (sec).

<Fiber Specific Gravity>

The fiber specific gravity (g/cm³) of pulp was measured according to JIS M 8717, using a He gas comparative densitometer (manufactured by Tokyo Science Co., Ltd.).

<Apparent Bulk Density>

After layering 10 g of ground pulp at 100 mm×100 mm, a 100 mm×100 mm plate was laid thereover and a weight with a 100 g load was set on the plate. The thickness of the layered pulp at 10 seconds after placement of the weight was used as the apparent bulk (cm³), and the apparent bulk density (g/cm³) was calculated.

<Fluid Absorption, Fluid Absorption Under Pressure, Fluid Retention>

(a) After placing 1000 mL of 0.9% physiological saline in a 2 L beaker, the liquid temperature was measured. The 0.9% physiological saline was prepared by placing 27.0 g of sodium chloride (extra pure reagent grade) in a 3 L beaker, and then adding ion-exchanged water to the 3 L beaker until the total amount of ion-exchanged water and sodium chloride reached 3000 g.

Figure 4:
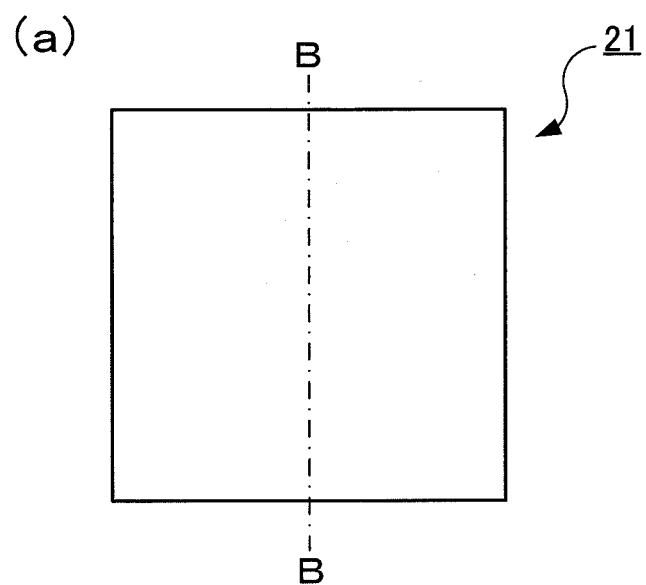
FIGS. 4(a) and 4(b) is a diagram for illustration of a nylon mesh bag to be used for measurement of fluid absorption.
Figure 4:
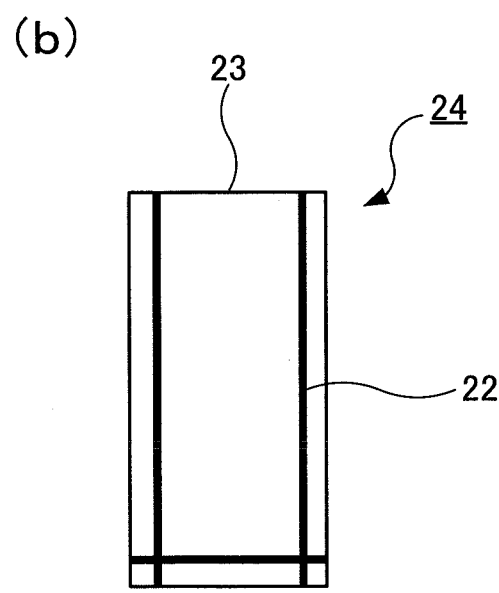

(b) A 250-mesh nylon mesh (N-NO. 250HD by NBC Industries) was cut to a size of 200 mm×200 mm (nylon mesh 21 shown in FIG. 4(a)) and the weight (x(g)) was measured, after which it was folded at the section of the dotted line B-B as shown in FIG. 4(a) to fold the nylon mesh 21 in half. As shown in FIG. 4(b), it was placed with the folded section at the right, and then heat seals 22 were formed at a location 5 mm above the bottom edge, a location 5 mm to the left of the right edge and a location 5 mm to the right of the left edge, to form a nylon mesh bag 24 with an open top edge 23. The sample (y(g)) whose weight had been previously measured was placed in the nylon mesh bag 24, and a heat seal (not shown) was formed to close the open top edge 23 of the nylon mesh bag 24.

(c) The bag containing the sample was completely dipped into 0.9% physiological saline, and allowed to stand for 3 minutes.

(d) After standing, the bag containing the sample was lifted, and it was allowed to stand naturally for draining for a period of 3 minutes.

(e) The weight ($z_1$ (g)) of the sample-containing bag was measured.

(f) The fluid absorption under a normal condition (non-pressure condition) was calculated from the following formula.

$$\text{Fluid absorption (g/g)} = ((z_1-x)-y)/y$$

(g) Following (e), an acrylic board was placed on the sample-containing bag, and on the acrylic board there was further placed a weight as a 3.5 kg load per 100 mm×100 mm, and allowed to stand for 3 minutes.

(h) The weight and acrylic board were removed, and the weight of the sample-containing bag ($z_2$ (g)) was measured.

(i) The fluid absorption under pressure was calculated from the following formula.

$$\text{Fluid absorption under pressure (g/g)} = ((z_2-x)-y)/y$$

(j) Following (h), the sample-containing bag was dehydrated with a centrifugal separator. The centrifugal separator used for this was a Model H130 separator by Kokusan Centrifugation Co., Ltd. The rotational speed of the centrifugal separator was 850 rpm (150 G).

(k) After the dewatering, the weight ($z_3$ (g)) of the sample-containing bag was measured.

(l) The fluid retention was calculated by the following formula.

$$\text{Fluid retention (g/g)} = ((z_3-x)-y)/y$$

The mean fiber size (μm), lignin content (wt %), settling time (sec), fiber specific gravity (g/cm³), apparent bulk density (g/cm³), fluid absorption (g/g), fluid absorption under pressure (g/g) and fluid retention (g/g) of the ground pulps 1 to 7 are shown in Table 1.

TABLE 1

| Ground pulp | Type of starting material | Type of pulp | Mean fiber size (μm) | Lignin content (wt %) | Settling time (sec) | Fiber specific gravity (g/cm³) | Apparent bulk density (g/cm³) | Fluid absorption (g/g) | Fluid absorption under pressure (g/g) | Fluid retention (g/g) |
|---|---|---|---|---|---|---|---|---|---|---|
| 1 | Abaca (near core) | Abaca BKP (AK104) | 17.9 | <0.2 | 3.30 | 1.52 | 0.054 | 25.7 | 19.0 | 7.8 |
| 2 | Abaca (middle) | Abaca BKP (AK102) | 18.0 | <0.2 | 3.32 | 1.57 | 0.065 | 22.5 | 18.8 | 7.7 |
| 3 | Abaca (near hull) | Abaca BKP (AK101) | 19.8 | 0.3 | 3.50 | 1.54 | 0.067 | 19.1 | 17.6 | 7.6 |
| 4 | Banana (stem) | Banana BKP | 12.5 | 0.3 | 2.84 | 1.46 | 0.048 | 25.9 | 13.9 | 8.2 |
| 5 | Conifer (Douglas fir) | Wood pulp (NBKP) | 34.5 | <0.2 | 1.04 | 1.45 | 0.083 | 16.2 | 12.0 | 8.4 |
| 6 | Sugar cane (bagasse) | Bagasse BKP | 12.6 | <0.2 | 1.26 | 1.50 | 0.061 | 18.8 | 16.0 | 8.3 |

TABLE 1-continued

| Ground pulp | Type of starting material | Type of pulp | Mean fiber size (μm) | Lignin content (wt %) | Settling time (sec) | Fiber specific gravity (g/cm³) | Apparent bulk density (g/cm³) | Fluid absorption (g/g) | Fluid absorption under pressure (g/g) | Fluid retention (g/g) |
|---|---|---|---|---|---|---|---|---|---|---|
| 7 | Kenaf (bast) | Kenaf BKP | 12.6 | <0.2 | 1.82 | 1.50 | 0.059 | 19.2 | 12.3 | 8.4 |

Ground pulps 1, 2 and 4 (abaca BKP (AK104 and 102) and banana BKP) satisfied all of the following properties, but the other ground pulps failed to satisfy one or more of the properties.

A settling time in water of 2 to 5 seconds.
An apparent bulk density of 0.04 to 0.07 g/cm³.
An artificial urine absorption of at least 20 times the mass of pulp.
A mean fiber size of 8 to 25 μm.
A lignin content of 0.5 mass % or less.

Also, the fluid absorption under a normal condition (non-pressure condition) and fluid absorption under pressure of the ground pulps 1, 2 and 4 (abaca BKP (AK104 and 102) and banana BKP) were superior to those of the ground pulp 5 (wood pulp (NBKP)), but the fluid retention of the ground pulps 1, 2 and 4 was about the same as or inferior to that of ground pulp 5.

Figure 5:
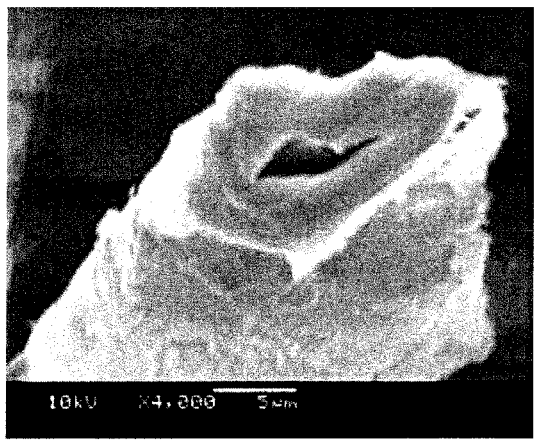
FIGS. 5(a), 5(b) and 5(c) is a scanning electron micrograph of a cross-section of a ground pulp fiber.
Figure 5:
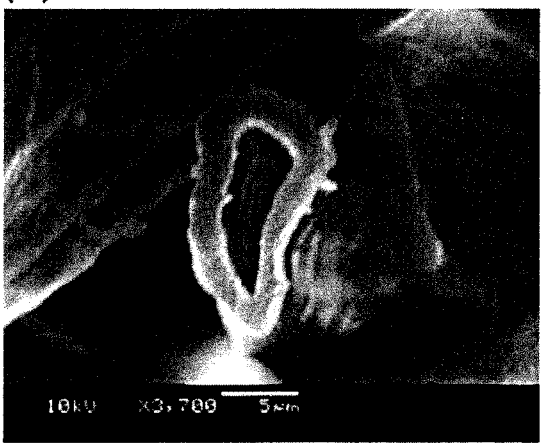
Figure 5:
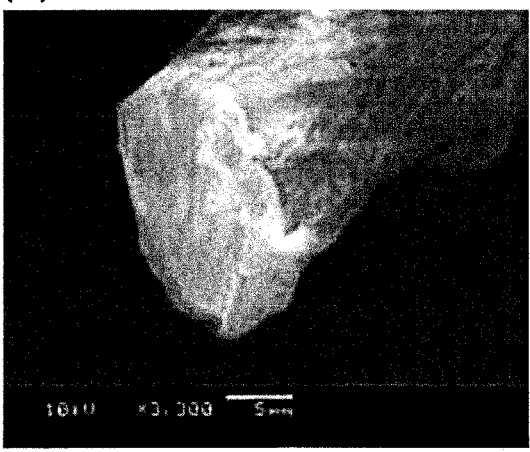

These properties of the abaca pulp and banana pulp are presumably due to the following reasons. FIG. 5 shows scanning electron microscope (SEM) photographs of cross-sections of a fiber of abaca pulp, banana pulp and wood pulp, respectively. FIG. 5(a) is a SEM photograph of the cross-section of an abaca pulp fiber, FIG. 5(b) is a SEM photograph of the cross-section of a banana pulp fiber, and FIG. 5(c) is a SEM photograph of the cross-section of a wood pulp fiber. As shown in FIG. 5, abaca pulp and banana pulp have a porous structure (hollow structure), whereas wood pulp does not have a porous structure (hollow structure). Since abaca pulp and banana pulp can take up fluids into the voids of the porous structure, they are expected to have excellent fluid absorption and fluid retention under pressure.

Examples 1 to 5 and Comparative Examples 1 to 5

(1) Preparation of Example Product 1

Mixed material 1 was prepared by evenly mixing ground pulp 1 (abaca BKP (AK104)), ground pulp 5 (wood pulp (NBKP)) and SAP (product of Sumitomo Seika Chemicals Co., Ltd., AQUA KEEP SA60S) to respective basis weights of 188 g/m² (ground pulp 1), 62 g/m² (ground pulp 5) and 250 g/m² (SAP). Tissue (basis weight: 16 g/m²) was set on the inner side of a wooden frame (length: 100 mm, width: 100 mm), and the mixed material 1 was layered on the tissue. The layered product of the tissue and mixed material 1 was removed, and a separate tissue (basis weight: 16 g/m²) was placed on the mixed material 1, to prepare an absorber 1 covered with a tissue. An air-through nonwoven fabric (length: 100 mm, width: 100 mm, basis weight: 25 g/m²) was set on the top surface side of the absorber 1 as a surface sheet, to prepare an absorbent article sample (Example Product 1).

(2) Preparation of Example Product 2

Mixed material 2 was prepared by evenly mixing ground pulp 1 (abaca BKP (AK104)), ground pulp 5 (wood pulp (NBKP)) and SAP (product of Sumitomo Seika Chemicals Co., Ltd., AQUA KEEP SA60S) to respective basis weights of 125 g/m² (ground pulp 1), 125 g/m² (ground pulp 5) and 250 g/m² (SAP), and the mixed material 2 was used to prepare an absorbent article sample (Example Product 2) in the same manner as Example Product 1.

(3) Preparation of Example Product 3

Mixed material 3 was prepared by evenly mixing ground pulp 1 (abaca BKP (AK104)), ground pulp 5 (wood pulp (NBKP)) and SAP (product of Sumitomo Seika Chemicals Co., Ltd., AQUA KEEP SA60S) to respective basis weights of 62 g/m² (ground pulp 1), 188 g/m² (ground pulp 5) and 250 g/m² (SAP), and the mixed material 3 was used to prepare an absorbent article sample (Example Product 3) in the same manner as Example Product 1.

(4) Preparation of Example Product 4

Mixed material 4 was prepared by evenly mixing ground pulp 4 (banana BKP), ground pulp 5 (wood pulp (NBKP)) and SAP (product of Sumitomo Seika Chemicals Co., Ltd., AQUA KEEP SA60S) to respective basis weights of 125 g/m² (ground pulp 4), 125 g/m² (ground pulp 5) and 250 g/m² (SAP), and the mixed material 4 was used to prepare an absorbent article sample (Example Product 4) in the same manner as Example Product 1.

(5) Preparation of Example Product 5

Mixed material 5 was prepared by evenly mixing ground pulp 1 (abaca BKP (AK104)), ground pulp 5 (wood pulp (NBKP)) and SAP (product of Sumitomo Seika Chemicals Co., Ltd., AQUA KEEP SA60S) to respective basis weights of 75 g/m² (ground pulp 1), 75 g/m² (ground pulp 5) and 350 g/m² (SAP), and the mixed material 5 was used to prepare an absorbent article sample (Example Product 5) in the same manner as Example Product 1. The Example Product 5 has a higher SAP ratio than Example Products 1 to 4.

(6) Preparation of Comparative Example Product 1

Mixed material 6 was prepared by evenly mixing ground pulp 1 (abaca BKP (AK104)) and SAP (product of Sumitomo Seika Chemicals Co., Ltd., AQUA KEEP SA60S) to respective basis weights of 250 g/m² (ground pulp 1) and 250 g/m² (SAP), and the mixed material 6 was used to prepare an absorbent article sample (Comparative Example Product 1) in the same manner as Example Product 1.

(7) Preparation of Comparative Example Product 2

Mixed material 7 was prepared by evenly mixing ground pulp 5 (wood pulp (NBKP)) and SAP (product of Sumitomo Seika Chemicals Co., Ltd., AQUA KEEP SA60S) to respective basis weights of 250 g/m² (ground pulp 5) and 250 g/m² (SAP), and the mixed material 7 was used to prepare an absorbent article sample (Comparative Example Product 2) in the same manner as Example Product 1.

(8) Preparation of Comparative Example Product 3

Mixed material 8 was prepared by evenly mixing ground pulp 3 (abaca BKP (AK101)), ground pulp 5 (wood pulp (NBKP)) and SAP (product of Sumitomo Seika Chemicals Co., Ltd., AQUA KEEP SA60S) to respective basis weights of 125 g/m² (ground pulp 3), 125 g/m² (ground pulp 5) and 250 g/m² (SAP), and the mixed material 8 was used to prepare an absorbent article sample (Comparative Example Product 3) in the same manner as Example Product 1.

(9) Preparation of Comparative Example Product 4

Mixed material 9 was prepared by evenly mixing ground pulp 7 (kenaf BKP), ground pulp 5 (wood pulp (NBKP)) and SAP (product of Sumitomo Seika Chemicals Co., Ltd., AQUA KEEP SA60S) to respective basis weights of 125 g/m² (ground pulp 7), 125 g/m² (ground pulp 5) and 250 g/m² (SAP), and the mixed material 9 was used to prepare an absorbent article sample (Comparative Example Product 4) in the same manner as Example Product 1.

(10) Preparation of Comparative Example Product 5

Mixed material 10 was prepared by evenly mixing ground pulp 5 (wood pulp (NBKP)) and SAP (product of Sumitomo Seika Chemicals Co., Ltd., AQUA KEEP SA60S) to respective basis weights of 150 g/m² (ground pulp 5) and 350 g/m² (SAP), and the mixed material 10 was used to prepare an absorbent article sample (Comparative Example Product 5) in the same manner as Example Product 1. The Comparative Example Product 5 has a higher SAP ratio than Comparative Example Products 1 to 4.

(11) Evaluation test for Example Products 1 to 5 and Comparative Example Products 1 to 5

The weights and thicknesses of the absorbers of Example Products 1 to 5 and Comparative Example Products 1 to 5 were measured in the following manner.

<Weight and Thickness>

After evenly blowing 0.1 g of atomized water onto the entire surface sheet of the absorbent article and using a pressing machine to evenly apply a 4 MPa load to produce a fixed density, a thickness gauge (Model J-B by Peacock, springless) was used to measure the weight (g) and thickness (mm) of the absorber.

The absorption times and rewetting amounts of Example Products 1 to 5 and Comparative Example Products 1 to 5 were measured in the following manner. The fluid absorption and fluid absorption under pressure were also measured in the same manner as the test example described above.

<Absorption Time and Rewetting Amount>

(a) A cylinder (inner diameter: 600, height: 50 mm) was set on the surface sheet of the absorbent article (the section corresponding to the center section of the absorber).

(b) 40 mL of 0.9% physiological saline solution (hereunder, "artificial urine") was injected into the cylinder at an injection rate of 8 mL/sec.

(c) The time from initial injection of the artificial urine until the artificial urine was absorbed into the absorbent article and disappeared from the cylinder (sec) was measured and recorded as the absorption time 1 (sec). Since 5 seconds is necessary for injection of 40 mL of artificial urine, an absorption time closer to 5 seconds indicates a higher absorption rate.

(d) At 5 minutes after initial injection of the artificial urine, additional 40 mL of artificial urine was injected at an injection rate of 8 mL/sec, and the time until disappearance from the cylinder (sec) was measured in the same manner as for the absorption time 1, and recorded as the absorption time 2 (sec).

(e) After an additional 5 minutes elapsed, the cylinder was removed from the absorbent article, and approximately 50 g of previously weighed filter paper (100 mm×100 mm) was set at the location where the cylinder had been set, and a weight applying a 3.5 kg load per 100 mm×100 mm was placed on the filter paper.

(f) At 3 minutes after placement of the weight, the filter paper was recovered and the weight of the filter paper was measured. The amount of artificial urine absorbed into the filter paper was calculated from the weight of the filter paper before and after placement on the absorbent article, and this was recorded as the rewetting amount (g).

The absorption time 1, absorption time 2, rewetting amount, fluid absorption and fluid absorption under pressure of each of Example Products 1 to 5 and Comparative Example Products 1 to 5 are shown in Table 2.

TABLE 2

| | Absorber properties | Example product | | | | | Comp. Example product | | | | |
|---|---|---|---|---|---|---|---|---|---|---|---|
| | | 1 | 2 | 3 | 4 | 5 | 1 | 2 | 3 | 4 | 5 |
| Component ratio (wt %) | Ground pulp 1 (Abaca 104) | 37.5 | 25 | 12.5 | | 15 | 50 | | | | |
| | Ground pulp 3 (Abaca 101) | | | | | | | | 25 | | |
| | Ground pulp 7 (Kenaf) | | | | | | | | | 25 | |
| | Ground pulp 4 (Banana) | | | | 25 | | | | | | |
| | Ground pulp 5 (Wood pulp) | 12.5 | 25 | 37.5 | 25 | 15 | | 50 | 25 | 25 | 30 |
| | SAP | 50 | 50 | 50 | 50 | 70 | 50 | 50 | 50 | 50 | 70 |
| Basis weight (g/m²) | Non-wood pulp | 188 | 125 | 62 | 125 | 75 | 250 | | 125 | 125 | |
| | Wood pulp | 62 | 125 | 188 | 125 | 75 | | 250 | 125 | 125 | 150 |
| | SAP | 250 | 250 | 250 | 250 | 350 | 250 | 250 | 250 | 250 | 350 |
| | Surface sheet | 25 | 25 | 25 | 25 | 25 | 25 | 25 | 25 | 25 | 25 |
| | Upper tissue | 16 | 16 | 16 | 16 | 16 | 16 | 16 | 16 | 16 | 16 |
| | Lower tissue | 16 | 16 | 16 | 16 | 16 | 16 | 16 | 16 | 16 | 16 |
| | Total basis weight | 557 | 557 | 557 | 557 | 557 | 557 | 557 | 557 | 557 | 557 |
| Size (mm) | | 100 × 100 | 100 × 100 | 100 × 100 | 100 × 100 | 100 × 100 | 100 × 100 | 100 × 100 | 100 × 100 | 100 × 100 | 100 × 100 |

TABLE 2-continued

| Absorber properties | Example product | | | | | Comp. Example product | | | | |
|---|---|---|---|---|---|---|---|---|---|---|
| | 1 | 2 | 3 | 4 | 5 | 1 | 2 | 3 | 4 | 5 |
| Weight (g) | 5.4 | 5.7 | 5.7 | 5.7 | 6.1 | 5.4 | 5.9 | 5.4 | 5.7 | 6.1 |
| Thickness (mm) | 4.3 | 4.0 | 4.0 | 4.0 | 4.1 | 4.0 | 4.5 | 4.0 | 4.3 | 3.8 |
| Density (g/cm³) | 0.13 | 0.14 | 0.14 | 0.14 | 0.14 | 0.14 | 0.12 | 0.14 | 0.13 | 0.15 |
| Test results | | | | | | | | | | |
| Absorption time 1 (sec) | 8.9 | 8.9 | 8.9 | 7.9 | 8.9 | 8.7 | 8.8 | 8.9 | 8.5 | 10.6 |
| Absorption time 2 (sec) | 8.3 | 9.0 | 9.7 | 7.8 | 8.3 | 7.8 | 12.5 | 11.6 | 12.2 | 11.2 |
| Rewetting amount (g) | 12.9 | 11.8 | 13.1 | 10.2 | 0.6 | 13.9 | 13.8 | 13.0 | 12.5 | 1.3 |
| Fluid absorption (g/g) | 30.4 | 29.8 | 27.7 | 29.5 | 32.9 | 30.0 | 27.0 | 28.7 | 27.7 | 32.8 |
| Fluid absorption under pressure (g/g) | 23.0 | 22.9 | 21.8 | 21.3 | 27.8 | 21.9 | 20.2 | 21.8 | 20.9 | 26.7 |

When Example Products 1 to 4 are compared with Comparative Example Product 1, despite all having a total pulp content of 50 wt %, the fluid absorptions and fluid absorptions under pressure were about the same, or those of Example Products 1 to 4 were greater, while the rewetting amounts and absorption time 2 values were about the same, or those of Example Products 1 to 4 were smaller. This demonstrated that when non-wood pulp (abaca BKP (AK104) and banana BKP) and wood pulp (NBKP) were blended, the fluid absorption under a normal condition (non-pressure condition), the fluid absorption under pressure, the fluid retention and the fluid absorption after repeated absorption of fluids were improved compared to non-wood pulp alone.

When Example Products 1 to 4 are compared with Comparative Example Product 2, despite all having a total pulp content of 50 wt %, the fluid absorptions and the fluid absorptions under pressure were greater with Example Products 1 to 4, and the rewetting amounts and the absorption time 2 values were smaller with Example Products 1 to 4. Also, when Example Product 5 is compared with Comparative Example Product 5, despite all having a total pulp content of 30 wt %, the fluid absorptions and the fluid absorptions under pressure were about the same, or those of Example Product 5 were greater, while the rewetting amounts, the absorption time 1 values and the absorption time 2 values were smaller with Example Products 1 to 4. This demonstrated that when non-wood pulp (abaca BKP (AK104) and banana BKP) and wood pulp (NBKP) are blended, the fluid absorption under a normal condition (non-pressure condition), the fluid absorption under pressure, the fluid retention and the fluid absorption after repeated absorption of fluids were improved compared to wood pulp alone.

When Example Products 1 to 4 are compared with Comparative Example Products 3 and 4, despite all having a total pulp content of 50 wt %, the fluid absorptions and the fluid absorptions under pressure were about the same, or those of Example Products 1 to 4 were greater, while the rewetting amounts and the absorption time 2 values were about the same, or those of Example Products 1 to 4 were smaller. This demonstrated that when the non-wood pulp blended with the wood pulp was abaca BKP (AK104) or banana BKP, the fluid absorption under a normal condition (non-pressure condition), the fluid absorption under pressure, the fluid retention and the fluid absorption after repeated absorption of fluids were improved compared to when it was other non-wood pulp.

EXPLANATION OF SYMBOLS

1 Disposable diaper (absorbent article)
2 Liquid-permeable sheet
3 Liquid-impermeable sheet
5 Absorber

The invention claimed is:

1. An absorber, comprising,
non-wood pulp having a hollow structure; and
wood pulp having no hollow structure,
wherein
the absorber has a thickness in a range of 3 to 7 mm and a density in a range of 0.05 to 0.3 g/cm³,
a settling time in water of the non-wood pulp is 2 to 5 seconds, and
the non-wood pulp is abaca pulp made from Manila hemp leaf sheath, or banana pulp made from banana stem.

2. The absorber according to claim 1, wherein an apparent bulk density of the non-wood pulp is 0.04 to 0.07 g/cm³.

3. The absorber according to claim 1, wherein an artificial urine absorption of the non-wood pulp is at least 20 times a mass of the non-wood pulp, the artificial urine absorption being measured with an artificial urine including 0.9% physiological saline.

4. The absorber according to claim 1, wherein a mean fiber size of the non-wood pulp is 8 to 25 µm.

5. The absorber according to claim 1, wherein a lignin content of the non-wood pulp is 0.5 mass % or less.

6. The absorber according to claim 1, wherein the abaca pulp is abaca pulp made from a portion near a core of the Manila hemp leaf sheath or from a portion between the core and a hull of the Manila hemp leaf sheath.

7. The absorber according to claim 1, wherein a mass ratio of the non-wood pulp to the wood pulp is 3:1 to 1:3.

8. The absorber according to claim 1, wherein a total content of the non-wood pulp and the wood pulp is at least 30 mass % of the absorber.

9. The absorber according to claim 1, further comprising an absorbent polymer.

10. The absorber according to claim 1, wherein when after 40 mL of artificial urine is absorbed into the absorber, additional 40 mL of artificial urine is added to the absorber at a rate of 8 mL/sec, an absorption time for the absorber to absorb the additional mL of the artificial urine is 10 seconds or shorter, and
the artificial urine includes 0.9% physiological saline.

11. The absorber according to claim 1, wherein the non-wood pulp is the abaca pulp made from the Manila hemp leaf sheath.

12. The absorber according to claim 1, wherein the non-wood pulp is the banana pulp made from the banana stem.

13. The absorber according to claim 1, wherein
an apparent bulk density of the non-wood pulp is 0.04 to 0.07 g/cm³,
a mean fiber size of the non-wood pulp is 8 to 25 µm, and
a lignin content of the non-wood pulp is 0.5 mass % or less.

14. An absorbent article, comprising:
a liquid-permeable sheet;
a liquid-impermeable sheet; and
an absorber situated between the liquid-permeable sheet and the liquid-impermeable sheet,
wherein
the absorber has a thickness in a range of 3 to 7 mm and a density in a range of 0.05 to 0.3 g/cm$^3$,
the absorber includes
non-wood pulp having a hollow structure; and
wood pulp having a non-hollow structure,
wherein
a settling time in water of the non-wood pulp is 2 to 5 seconds, and
the non-wood pulp is abaca pulp made from Manila hemp leaf sheath, or banana pulp made from banana stem.

15. The absorbent article according to claim 14, wherein the non-wood pulp is the abaca pulp made from the Manila hemp leaf sheath.

16. The absorbent article according to claim 14, wherein the non-wood pulp is the banana pulp made from the banana stem.

17. The absorbent article according to claim 14, wherein
an apparent bulk density of the non-wood pulp is 0.04 to 0.07 g/cm$^3$,
a mean fiber size of the non-wood pulp is 8 to 25 μm, and
a lignin content of the non-wood pulp is 0.5 mass % or less.

18. The absorbent article according to claim 17, wherein the abaca pulp is abaca pulp made from a portion near a core of the Manila hemp leaf sheath or from a portion between the core and a hull of the Manila hemp leaf sheath.

19. The absorbent article according to claim 18, wherein a mass ratio of the non-wood pulp to the wood pulp is 3:1 to 1:3, and a total content of the non-wood pulp and the wood pulp is at least 30 mass % of the absorber.

20. The absorber according to claim 13, wherein a mass ratio of the non-wood pulp to the wood pulp is 3:1 to 1:3, and a total content of the non-wood pulp and the wood pulp is at least 30 mass % of the absorber.

* * * * *